United States Patent [19]

Hadden et al.

[11] 4,387,226
[45] Jun. 7, 1983

[54] PURINE-DIHYDROTHIAZOLES

[75] Inventors: John W. Hadden, New York, N.Y.; Lionel N. Simon, Santa Ana, Calif.; Alfredo Giner-Sorolla, Riverside, Conn.

[73] Assignees: Newport Pharmaceuticals International, Inc., Newport Beach, Calif.; Sloan-Kettering Institute For Cancer Research, New York, N.Y.

[21] Appl. No.: 296,557

[22] Filed: Aug. 26, 1981

[51] Int. Cl.³ .................. C07D 473/22; C07D 473/30; C07D 473/38; A61K 31/52
[52] U.S. Cl. .................................. 544/247; 544/251; 424/253
[58] Field of Search ................ 544/247, 251; 424/251, 424/253

[56] References Cited

U.S. PATENT DOCUMENTS

| 2,592,930 | 4/1952 | Matsukawa et al. | 544/251 X |
| 2,592,931 | 4/1952 | Matsukawa et al. | 544/251 X |
| 3,637,684 | 1/1972 | Goldman | 424/253 X |
| 3,646,007 | 2/1972 | Gordon | 260/211.5 R |
| 3,770,741 | 11/1973 | Goldman | 242/253 X |

FOREIGN PATENT DOCUMENTS

| 51-6992 | 1/1976 | Japan | 544/251 |
| 233673 | 5/1969 | U.S.S.R. | 544/251 |

OTHER PUBLICATIONS

Hino, et al., Chemical Abstracts, vol. 83, 206208w (1975).
Uno, et al., Chemical Abstracts, vol. 80, 37,174n, 48,038x (1974).
Uno, et al., Chemical Abstracts, vol. 82, 140191f, vol. 83, 28191a (1975).
Ochiai, Chem. Ber., 69, pp. 1650-1655 (1936).
Gordon, J. Am. Chem. Soc. vol. 73, pp. 984-986 (1951).
Cacace, et al., Chemical Abstracts, vol. 51, 6655d (1957).
Elderfield, et al., Chemical Abstracts, vol. 54, 5666g (1960).
Balsiger, et al., Chemical Abstracts, vol. 57, 826b (1962).
Yurchenko, et al., Chemical Abstracts, vol. 78, 43424u (1973).
Marumoto, et al., Chemical Abstracts, vol. 81, 25885c (1974).
Alekseeva, et al., Chemical Abstracts, vol. 82, 16791n (1975).
Montgomery et al., J. Heterocyclic Chem., vol. 17, pp. 583-584.
Fenichel, et al., Journal of Immunopharmacology, 2 (4), pp. 491-508 (1980).
The Ring Index Supplement III, p. 122.

Primary Examiner—Donald G. Daus
Assistant Examiner—Diana G. Rivers
Attorney, Agent, or Firm—Cushman, Darby & Cushman

[57] ABSTRACT

There are prepared compound of the formulae

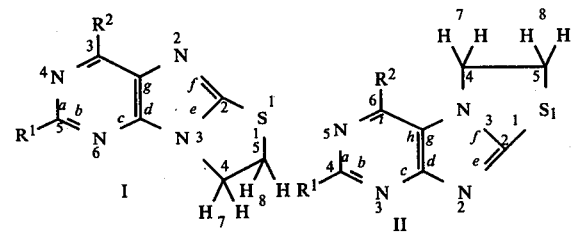

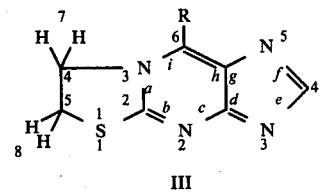

Where $R^1$ is H, lower alkyl S—, lower alkyl

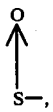

$NH_2$ or halogen, $R^2$ is OH, lower alkyl S—, halogen, $NH_2$ or SH R is OH, SH, lower alkyl S—, or halogen and
$R^3$ is OH, SH, lower alkyl S—, halogen or $NH_2$.

The compounds have antiviral and immunomodulating activity.

27 Claims, No Drawings

PURINE-DIHYDROTHIAZOLES

BACKGROUND OF THE INVENTION

The present invention is directed to novel substances intended to modulate the immune response drawn on the types of chemical entities previously demonstrated to have that type of activity. Isoprinosine ® (A), Gordon U.S. Pat. No. 3,646,007 is an immunomodulator demonstrated to have effects mainly on T-cells. Levamisole (B) has also been shown to have effects mainly on T-cells.

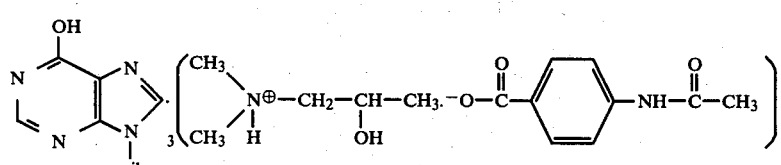

A

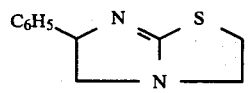

B

SUMMARY OF THE INVENTION

Applicants have devised a new series of compounds possessing some structural characteristics in common to both molecules. The resulting substances, the dihydrothiazolo purines are most interesting biologically, in that they do possess immunomodulating properties but quite unexpectedly have a much greater effect on stimulating the B-cell response; e.g. Ia, Ic, IIa, IVa, or inhibiting the T-cell response; e.g. Ib, as well as stimulating T-cell response.

Therefore, the results presented herein demonstrates that (1) novel derivatives of dihydrothiazolo purines can be prepared which (2) possess in vitro antiviral activity and (3) are capable of enhancing both the T- and B-cell responses or inhibiting the T-cell response.

Dihydrothiazolo purines within the invention include those within the formula I, II, and III below wherein for convenience the numbering system is also provided. It has also been found that the novel dihydrothiazolo compounds of formula IV below also have the same immunomodulating properties.

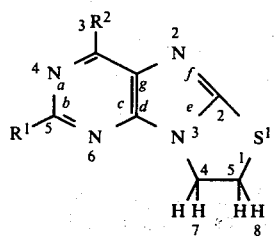

I

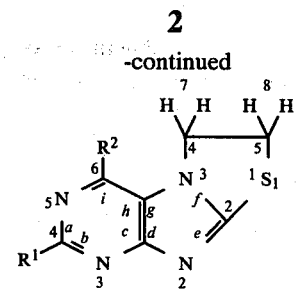

II

III

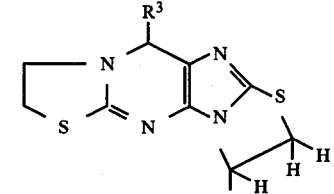

IV

In the formulae $R^1$ is hydrogen, lower alkylthio, e.g. methyl to butylthio, halogen, e.g. chlorine, bromine, or fluorine, lower alkylsulfinyl, e.g. methyl to butyl sulfinyl or amino, $R^2$ is hydroxy, lower alkyl thio, e.g. methyl to butylthio, amino, halogen, e.g. chlorine, bromine or fluorine, or mercapto, R is hydroxy, mercapto, lower alkyl thio, e.g. methyl to butylthio, halogen, e.g. chlorine, bromine, or fluorine and $R^3$ is hydroxy, mercapto, lower alkyl thio, e.g. methyl to butylthio, halogen, e.g. chlorine, bromine or fluorine or amino. Preferably $R^2$, $R^3$, and R are hydroxy. The presently most preferred compound has formula I with $R^1$ being hydrogen and $R^2$ being hydroxy.

A compound like the compounds of formula III with R being amino is disclosed in Montgomery, J. Heterocyclic Chem., Vol. 17, pages 583–584. It is used in Montgomery as an intermediate to make ethyladenine hydrobromide. No mention is made of antiviral or immunomodulating activities. Montgomery also shows a dihydrothiazolo purine having an amino group for $R^2$. However, this dihydrothiazolo purine has a significantly different structure than that of formula I, II, and III. Also the compound of Montgomery is only used as an intermediate to make ethyladenine.

Examples of compounds within the present invention are set forth in Tables 1 through IV below.

TABLE I

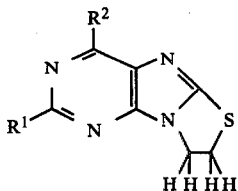

I

| COMPOUND | $R^1$ | $R^2$ |
|---|---|---|
| (a) 3-hydroxy-7,8-dihydrothiazolo-[3,2e]-purine (NPT 16416) | H | OH |
| (b) 3-methylmercapto-7,8-dihydro-thiazolo-[3,2e]-purine (NPT 16439) | H | $SCH_3$ |
| (c) 3-hydroxy-5-methylmercapto-7,8-dihydrothiazolo-[3,2e]-purine (NPT 16472) | $SCH_3$ | OH |
| (d) 3-amino-7,8-dihydrothiazolo-[3,2e]-purine (NPT 16422) | H | $NH_2$ |
| (e) 3-mercapto-7,8-dihydrothiazolo-[3,2]-purine | H | SH |
| (f) 3-chloro-7,8-dihydrothiazolo-[3,2e]-purine | H | Cl |
| (g) 3-hydroxy-5-methylsulfinyl-7,8-dihydrothiazolo-[3,2e]-purine | $CH_3-\overset{O}{\underset{\uparrow}{S}}$ | OH |
| (h) 3-hydroxy-5-amino-7,8-dihydro-thiazolo-[3,2e]-purine | $NH_2$ | OH |
| (i) 3-hydroxy-5-fluoro-7,8-dihydro-thiazolo-[3,2e]-purine | F | OH |
| (j) 3,5-diamino-7,8-dihydrothiazolo-[3,2e]-purine | $NH_2$ | $NH_2$ |
| (k) 3-mercapto-5-amino-7,8-dihydro-thiazolo-[3,2e]-purine | $NH_2$ | SH |

TABLE II

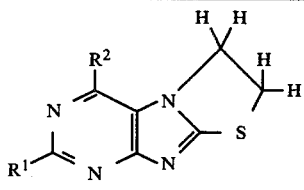

II

| COMPOUND | $R^1$ | $R^2$ |
|---|---|---|
| (a) 6-hydroxy-7,8-dihydrothiazolo-[2,3f]-purine (NPT 16485) | H | OH |
| (b) 5-methylmercapto-7,8-dihydro-thiazolo-[2,3f]-purine | H | $SCH_3$ |
| (c) 6-mercapto-7,8-dihydrothiazolo-[2,3f]-purine | H | SH |
| (d) 6-chloro-7,8-dihydrothiazolo-[2,3f]-purine | H | Cl |
| (e) 5-methylsulfinyl-6-hydroxy-7,8-dihydrothiazolo-[2,3f]-purine | $CH_3-\overset{O}{\underset{\uparrow}{S}}$ | OH |
| (f) 5-amino-6-hydroxy-7,8-dihydro-thiazolo-[2,3f]-purine | $NH_2$ | OH |
| (g) 5-fluoro-6-hydroxy-7,8-dihydro-thiazolo-[2,3f]-purine | F | OH |
| (h) 5,6 diamino-7,8-dihydrothiazolo-[2,3f]-purine | $NH_2$ | $NH_2$ |

TABLE II-continued

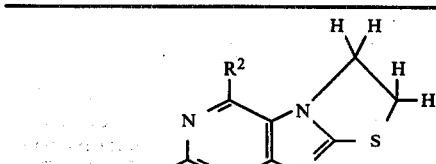

II

| COMPOUND | $R^1$ | $R^2$ |
|---|---|---|
| (i) 5-amino-6-mercapto-7,8-dihydro-thiazolo-[2,3f]-purine | $NH_2$ | SH |
| (j) 5-methylmercapto-6-hydroxy-7,8-dihydrothiazolo-[2,3f]-purine | $SCH_3$ | OH |
| (k) 6-amino-7,8-dihydrothiazolo-[2,3f]-purine | H | $NH_2$ |

TABLE III

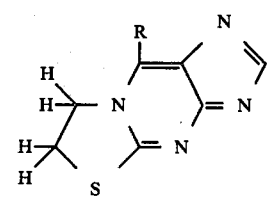

III

| COMPOUND | R |
|---|---|
| (a) 6-hydroxy-7,8-dihydrothiazolo-[3,2a]-purine (NPT 16450) | OH |
| (b) 6-mercapto-7,8-dihydrothiazolo-[3,2a]-purine | SH |
| (c) 6-mercaptomethyl-7,8-dihydro-thiazolo-[3,2a]-purine | $SCH_3$ |
| (d) 6-chloro-7,8-dihydrothiazolo-[3,2a]-purine | Cl |

TABLE IV

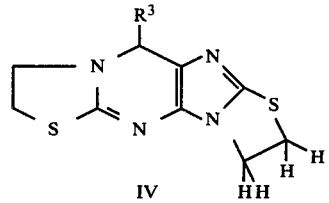

IV

| COMPOUND | $R^3$ |
|---|---|
| (a) 6-hydroxy-Bis-(3,4-dihydrothiazolo-8,9-dihydrothiazolo)-[3,2e-2,3a] purine (NPT 16449) | OH |
| (b) 6-mercapto-Bis-(3,4-dihydrothiazolo-8,9-dihydrothiazolo)-[3,2e-2,3a] purine | SH |
| (c) 6-methylmercapto-Bis-(3,4-dihydrothiazolo-8,9-dihydrothiazolo)-[3,2e-2,3a] purine | $SCH_3$ |
| (d) 6-chloro-Bis-(3,4-dihydrothiazolo-8,9-dihydrothiazolo)-[3,2e-2,3f] purine | Cl |
| (e) 6-amino-Bis-(3,4-dihydrothiazolo-8,9-dihydrothiazolo)-[3,2e-2,3f] purine | $NH_2$ |

The following table (Table V) summarizes the physical chemical properties of representative examples of the subject compounds of this invention.

TABLE V

CHEMICAL PROPERTIES OF REPRESENTATIVE EXAMPLES OF COMPOUNDS

| | M. wt. | M.p. C.° | C.H.N. Theory | Fd. | λmax/αm × 10³ pH. 1.0 | 7 | 9.5 | λmin 1 | 7 | TLC (Rf) | IR |
|---|---|---|---|---|---|---|---|---|---|---|---|
| NPT 16416 (Ia) | 194.22 | 341–3° | C 43.28 | 42.91 | 271/19.88 | 269/19.5 | 273/20.15 | | | A (0.4) | |
| | | | H 3.11 | 3.02 | | | | | | 1 spot | |
| | | | N 28.65 | 28.65 | | | | | | HPLC | |
| | | | S 16.51 | 16.46 | | | | | | 1 peak | |
| NPT 16472 (Ic) | 240.31 | 351–4 | C 39.98 | 39.82 | 236/28.37* | | | | | | |
| | | | H 3.35 | 3.33 | 274/15.34* | | | | | | |
| | | | N 23.31 | 23.26 | | | | | | | |
| (Methanol) | | | S 26.69 | 26.75 | | | | | | | |
| NPT 16439 (Ib) | 224.31 | 279 | C 42.83 | 42.80 | 256/14.37 | | | | | | |
| | | | H 3.59 | 3.53 | 340/27.5 | | | | | | |
| | | | N 24.97 | 24.86 | | | | | | | |
| | | | S 28.57 | 28.75 | | | | | | | |
| NPT 16485 (IIa) | 194.22 | 309(dec) | C 43.26 | 43.38 | 277/12.61 | 273/11.34 | 280.5/11.74 | 237 | 234 | A(0.57) | |
| | | | H 3.11 | 3.13 | | | | | | | |
| | | | N 28.85 | 28.90 | | | | | | | |
| | | | S 16.51 | 16.58 | | | | | | | |
| (23) | | | | | | | | | | | |
| NPT 16450 (IIIa) | 194.23 | 340°(dec) | C 43.06 | 43.76 | | 279/ | | | 233/ | | |
| | | | H 3.61 | 3.07 | | | | | | | |
| | | | N 28.70 | 28.78 | | | | | | | |
| | | | S 16.42 | 16.56 | | | | | | | |
| 16449 (V) | 252.33 | 303–5 | C 42.66 | 42.83 | 278/18.8 | 278/18.7 | 280/22.6 | | | | |
| | | 347 (dec) | H 3.58 | 3.19 | 235/32.4 | 235/32 | 227/22.6 | | | | |
| | | | N 22.11 | 22.06 | | | | | | | |
| | | | S 25.31 | 25.30 | | | | | | | |

The immunomodulators of the invention can be employed, for example, to provide resistance to invasion by the viruses in Table A.

TABLE A

| Virus | Class | Disease |
|---|---|---|
| Arenavirus | RNA | Rift Valley Fever |
| Influenza | RNA | Influenza |
| Rhinovirus | RNA | Common Cold |
| Polio | RNA | Polio |
| Measles | RNA | Rubella |
| Newcastle Disease Virus | RNA | Newcastle Disease |
| Rotavirus | RNA | Gastroenteritis in infants |
| Hepatitis Type A | RNA | Infectious Hepatitis |
| Rabies | RNA | Rabies |
| Arbovirus | RNA | Encephalitis |
| Vaccinia | DNA | Smallpox |
| Herpes Simplex | DNA | Cold sore, Encephalitis, Venereal Disease |
| Herpes Zoster | DNA | Shingles |
| Varicella Zoster | DNA | Chicken pox |
| Adenovirus | DNA | Respiratory |
| Hepatitis Type B | DNA | Chronic Hepatitis, Severe Hepatitis |
| Hoof and Mouth Disease | DNA | Hoof and Mouth Disease |
| Machupo | DNA | Hemorrhagic Fever |

The compounds and compositions of the invention are useful in treating mammals (and cells of mammals) including humans, swine, dogs, cats, cattle, horses, sheep, goats, mice, rabbits, rats, guinea pigs, hamsters, monkeys, etc.

Unless otherwise indicated, all parts and percentages are by weight.

All temperatures are in degrees centigrade unless otherwise indicated.

The composition can comprise, consist essentially of or consist of the materials set forth and the processes can comprise, consist essentially of or consist of the steps set forth with such materials.

The compositions can be administered to the mammals by conventional techniques, e.g., orally, nasally, rectally, vaginally, or parenterally. They can be employed as injectable solutions, e.g. in water, or as tablets, pills, capsules, etc.

DETAILED DESCRIPTION

The compounds of the invention can be prepared by the procedures set forth below:

Preparation of 3-substituted-7,8-dihydrothiazolo-[3,2e]-purines (Table I):

EXAMPLE 1

(a) 3, hydroxy-7,8-dihydrothiazolo-[3-2e]-purine (NPT 16416) Ia

Reaction of 8-mercaptohypoxanthine with ethylene dibromide

Method A

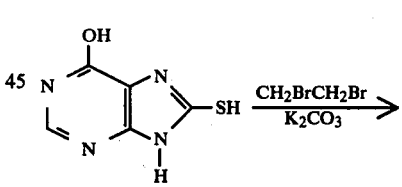

V

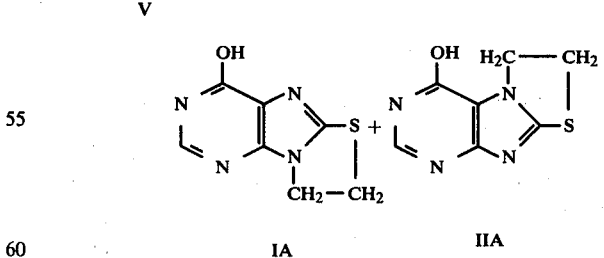

IA        IIA

To a suspension of 8-mercaptohypoxanthine (V, 6.3 g) in dimethylformamide (DMF) (69 ml), potassium carbonate (5.7 g) was added. Ethylene dibromide (3.75 ml) was then poured dropwise (ca. 5 min) and the reaction mixture was heated at 65°–70° C. for 4 hours. The u.v. was monitored at 1 hour intervals to check completion of reaction. After standing overnight at 25° C., the resulting suspension was filtered and washed with cold H₂O (2–3 times). The pH of the filtrate was adjusted to 6 with glacial acetic acid and evaporated to dryness in vacuo. A crude crystalline product was obtained: 5.27 g (78%); m.p. 270° C: u.v. λ max 269 nm (H₂O), 273 nm (OH⁻).

This product represents the mixture of the 2 compounds (compounds Ia and IIa in a ratio of 3:1). Repeated crystallization of the crude product from 30% aqueous ethanol yielded pure Ia.

Method B

Ethylene bromide (13.6 ml, 0.157 M) was added dropwise to a suspension of 8-mercaptohypoxanthine (V) (26.2 g, 0.1558 M) in DMF (550 ml) containing potassium carbonate (23.7 g, 0.171 M). The mixture was stirred at 55°–65° C. After 40 minutes the reaction was completed as judged by u.v. and t.l.c. analysis. The pH of the suspension was adjusted to 6.0 by addition of glacial acetic acid, the precipitate collected by filtration, washed twice with water (20 ml) and ethanol (1×20 ml) and dried in air at 25° C. This yielded 12.8 g (42%) of crude white crystalline material giving an Rf of 0.4 with a λ max at 27° nm. No IIa could be detected by thin layer chromatography (tlc). Recrystallization from 30% ethanol yielded pure Ia (NPT 16416). It appears that the use of a large amount of DMF (double volume) facilitates the solution and reaction of materials.

EXAMPLE 2

(b) 3-methylmercapto-7,8-dihydrothiazolo-(3,2e)-purine (NPT 16439) (Ib)

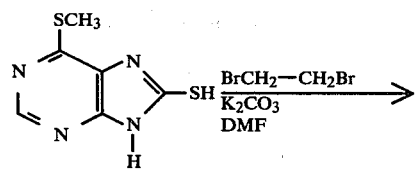

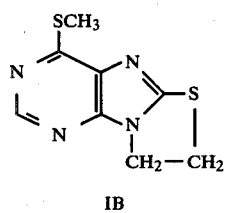

IB

A mixture of 6-methylmercapto-8-mercaptopurine (VI, 100 g) in DMF (875 ml), potassium carbonate (58 g) was stirred at 25° C. Ethylene dibromide (50 ml) was added dropwise. The reaction was heated at 70° C. for 5 hours and kept at 25° C. overnight. The precipitate was collected by filtration. A suspension in water was adjusted to pH 6 by the addition of glacial acetic acid. The precipitate was collected by filtration and washed with water to obtain a yellow crystalline product (Ib). Yield=92 g (81%), m.p. 279° C., u.v. pH=5.5 (λ max=236, λ sh 257, λ 309, λ 313).

The product was recrystallized from 70% ethanol. Anal. Calcd. for C₈H₈N₄S₂: C, 42.83; H, 3.59; N, 24.97; S, 28.57, Found: C, 42.80; H, 3.53; N, 24.86; S, 28.75

EXAMPLE 3

(c) 3-hydroxy-5-methylmercapto-7,8-dihydrothiazolo-[3,2e]-purine (NPT 16472) Ic.

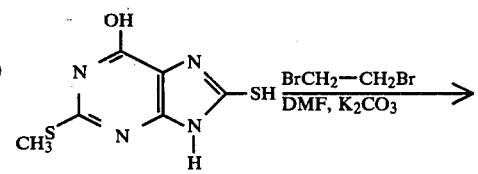

VII

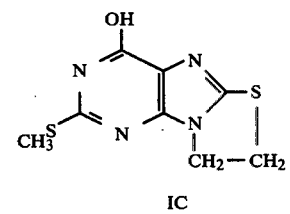

IC 1,2-dibromoethane (2.36 ml, 0.027 M) was added dropwise to a suspension of 2-methylmercapto-8-mercaptohypoxanthine (6.0 g, 0.028 M) in dimethylformamide (56 ml) containing potassium carbonate (3.86 g, 0.0280 M). The reaction mixture was heated at 65°–70° C. for 3 hours. After cooling, the pH of the mixture was adjusted to 5 with glacial acetic acid. The resulting precipitate was washed with H₂O (3×20 ml) and Et OH (1×20 ml) to yield a light cream colored crystalline material (Ic) u.v. λ max 235 and 280 nm (H₂O. Mp 298°–305° C. (dec.) Yield 5.0 g (75%).

Anal. Calcd. for C₈H₈N₄OS₂: C, 39.98; H, 3.35; N, 23.31; S, 26.69

Found: C, 39.82; H, 3.33; N, 23.26; S, 26.75

Synthesis of 6-substituted-7,8-dihydrothiazolo [2,3f] purines.

EXAMPLE 4

(a) 6-hydroxy-7,8-dihydrothiazolo[2,3f]-purines (NPT 16485) IIa

The mother liquors from the reaction described in Example 1, Method A, were evaporated to dryness in vacuo. The resulting crystalline white solid was recrystallized several times from 70% ethanol to yield pure IIa.

u.v., λ max 280.5 (pH 9.5); λ max 277 (pH 7.0); m.p. 309° C. (dec)

Rf. (ETOH. HAc. 1:1) 0.57

Anal. Calcd. for C₇H₆N₆OS: C, 43.28; H, 3.11; N, 28.85; S, 16.51

Found: C, 43.38; H, 3.13; N, 28.90; S, 16.58

Synthesis of 6-substituted-7,8-dihydrothiazolo[3,2a]-purines.

EXAMPLE 5

(a) 6-hydroxy-7,8-dihydrothiazolo-[3,2a]-purine (NPT 16450) IIIa.

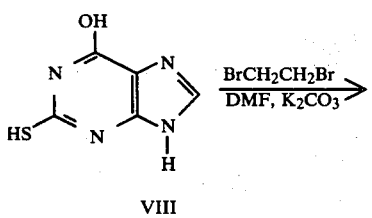

VIII

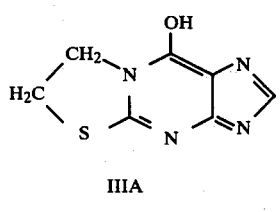

IIIA

To a mixture of 2-mercaptohypoxanthine (2 g) in DMF (40 ml), potassium carbonate was added (1.81 g). Ethylene dibromide (1.18 ml) was added slowly while stirring at 25° C. The reaction mixture was heated with stirring for 6 hours at 70° C. and then kept at 25° C. overnight. The resulting precipitate was collected by filtration, water was added to form a thick slurry and the pH was adjusted by the addition of glacial acetic acid. The precipitate was washed with a little water (4 times) to yield a yellow crystalline product (IIIa) yield=0.5 g, (21%), m.p. 340°, u.v., pH=5.5 (λ max=279 nm, λ min 233 nm).

An analytical sample was prepared by repeated recrystallization from 90% ethanol.

Anal. Calcd. for $C_7H_6N_4SO$: C, 43.29; H, 3.11; N, 28.85; S, 16.50.

Found: C, 43.76; H, 3.07; N, 28.78; S, 16.56.

Synthesis of Bis-(3,4-dihydrothiazolo-8,9-dihydrothiazolo)-[3,2e, 2,3f]-purines.

EXAMPLE 6

(a) Synthesis of 6-keto-(3,4-dihydrothiazolo-8,9-dihydrothiazolo)-[3,2e, 2,3f]-purines (NPT 16449) IVa.

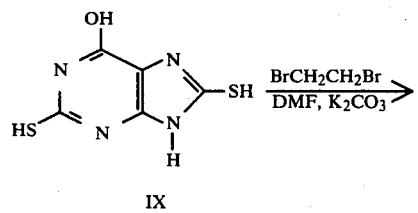

IX

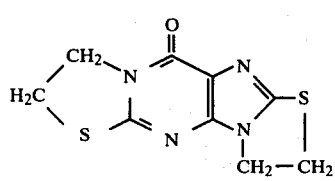

IVa

To a mixture of 2,8-mercaptohypoxanthine (IX) (2 g) in DMF (22 ml), potassium carbonate (3.62 g) was added. The mixture was stirred at 25° C. and ethylene dibromide (2.36 ml) was added dropwise. The temperature of the reaction rose a few degrees. After the addition was completed, the reaction was heated at 70° C. for 3 hours.

The suspension did not dissolve, although there was a transformation observed by U.V. After 3 hours, the reaction mixture was cooled and the precipitate (IVa) was collected by filtration, and then suspended in a minimum amount of water. The pH was adjusted to 6 by the addition of glacial acetic acid.

Yield 1.5 g (59%), m.p. 347° C., U.V. pH=5.5 (λ max 276, λ min 236). A sample was repeatedly recrystallized from 70% ethanol.

Anal. Calcd. for $C_9H_8N_4OS_2$: C, 42.84; H, 3.20; N, 22.21; S, 25.42.

Found: C, 42.83; H, 3.19; N, 22.06; S, 25.30.

STRUCTURE PROOF AND IDENTIFICATION OF NPT 16416 (Ia) AND NPT 16485 (IIa)

EXAMPLE 7

Raney nickel treatment of 7,8-dihydrothiazolo-[3,2-e] hypoxanthine (NPT 16416)

A suspension of 7,8-dihydrothiazolo-[3,2e]hypoxanthine (Ia, 30 mg) in $H_2O$ (15 ml) and conc. ammonium hydroxide (3 ml) and Raney Ni (ca. 20 mg) was refluxed for 24 hours. The suspension was filtered when hot, the Raney nickel washed with hot water, the filtrates combined, and evaporated to dryness in vacuo. The residue showed a u.v. λ max. 250 nm ($H_2O$, pH 5.5), 253 nm ($OH^-$), and 250 nm ($H^+$) indistinguishable from the one of 9-ethylhypoxanthine tlc. (silica gel, EtOAc: EtOH, 1:1) Rf, 0.37; spots on Whatman paper in 3 different solvent systems had the same Rf values as those of 9-ethylhypoxanthine.

EXAMPLE 8

Raney nickel treatment of 7,8-dihydrothiazole-[2,3-f]-hypoxanthine (NPT 16485 (IIa)

A suspension of 7,8-dihydrothiazolo-[2,3-f]hypoxanthine (IIa, 100 mg) in $H_2O$ (100 ml), conc. ammonia (3 ml) and Raney nickel (100 mg) was refluxed 24 hours. The suspension was filtered when hot, the Raney nickel washed with hot water and the combined filtrates evaporated to dryness in vacuo. A crystalline product (30 mg) was obtained. m.p. 255° C.; u.v. λ max. 256 nm ($H_2O$, pH 5.5), 260 nm ($OH^-$), 250 nm ($H^+$); tlc. (silica gel, EtOH:EtOAc, 1:1) Rf: 0.42.

BIOLOGICAL PROPERTIES

A. ANTIVIRAL ACTIVITY

The ability of NPT 16416 to inhibit influenza virus replication was measured using the hemadsorption assay. As can be seen noted from Table VI, NPT 16416 can cause a 48% to 78% inhibition of influenza virus (RNA virus) over the concentration range of 0.05 to 75 μg/ml. The inhibition of DNA virus replication is demonstrated in Table VI which shows that NPT 16416 can inhibit HSV replication by 33% to 65% over the concentration range of 37.5 to 150 μg/ml.

TABLE VI

EFFECTS OF NPT 16416 ON VIRAL REPLICATION

| VIRUS | % INHIBITION OF VIRAL GROWTH (CONC μg/ml) | | | | | |
|---|---|---|---|---|---|---|
| | 0.05 | 0.1 | 0.5 | 37.5 | 75 | 150 |
| Influenza A/USSR 90 | 48 | 54 | 59 | — | 78 | — |
| Herpes Simplex Virus Type I | — | — | — | 33 | 61 | 65 |

B. IMMUNOMODULATING ACTIVITY

The ability of the dihydrothiazolo purine derivatives of formula I, II, III, and IV to modulate the immune system has been demonstrated both in vitro and in vivo using the following systems:

Modulation of:

(1) Mitogen-(Lipopolysaccharide, LPS or Con A) induced lymphocyte proliferation using murine spleen cells (in vitro)

(2) Lymphokine (macrophage mitogenic factor, MMF) induced macrophage proliferation (in vitro (3) Antigen (sheep red blood cell, SRBC) dependent antibody synthesis (in vivo)

(4) Induction of theta positive cells in nude mice (in vitro).

1. The data presented in Table VII clearly demonstrates the ability of NPT 16416 to augment (from 30–180%) LPS induced lymphocyte proliferation. LPS is a mitogen which acts preferentially on B-cells. NPT 16416 has little or no effect on Con A induced proliferation (T-cells). NPT 16422 (Id) NPT 16439 (Ib) as seen by the data in Table IX clearly are potent inhibitors of Con A induced proliferation. Con A is considered a T-cell mitogen.

2. NPT 16416 is also capable of augmenting the lymphokine (MMF) induced proliferation of macrophages causing a 70% enhancement of macrophage proliferation.

3. The data in Tables VIII and X clearly show that NPT 16416 is capable of enhancing antibody production to SRBC in mice, to an extent of 88–226% at 0.05 mg/kg. NPT 16439 (Ib) is a potent inhibitor of antibody production.

less by the oral route since 500 mg/kg p.o. produced no deaths in Balb/c mice.

TABLE VIII

IMMUNOMODULATING PROPERTIES OF 3-HYDROXY-7,8-DIHYDROTHIAZOLO-[3,2e]-PURINE (NPT 16416): MODULATION OF Ig M ANITBODY PRODUCTION IN SRBC IMMUNIZED BALB/C MICE

| SUBSTANCE (DOSE-mg/kg) | #Ig M PLAQUES ($\bar{x} \pm$ S.E.) | % CHANGE FROM CONTROL |
|---|---|---|
| Saline Control | 21 ± 1.1 | — |
| NPT 16416 (Ia)-0.05 | 39 ± 3.34 | +88 |
| NPT 16416 (Ia)-0.5 | 35 ± 2.06 | +66 |
| NPT 16416 (Ia)-5.0 | 9 ± 0.37 | −58 |

TABLE IX

IMMUNOMODULATING PROPERTIES OF DIHYDROTHIAZOLO PURINES: COMPARISON OF IN VITRO LPS AND CON A INDUCED PROLIFERATION (MAXIMUM VALUES)

| COMPOUND (CON ng/ml) | CON A (.375 µg/ml) D/C* | LPS (5 µg/ml) |
|---|---|---|
| NPT 16416 (Ia) (1,000) | 1.18 | 2.01 |
| (25,000) | 1.18 | 2.36 |
| NPT 16485 (IIa) (25,000) | 1.18 | 1.85 |
| NPT 16450 (IIIa) (25,000) | 1.07 | 1.18 |
| NPT 16449 (IVa) (21,000) | 1.00 | 1.57 |
| NPT 16472 (Ic) (10) | 1.00 | 1.31 |
| NPT 16422 (Id) (25,000) | 0.20 | 0.37 |
| NPT 16439 (Ib) (4,500) | 0.57 | 1.0 |

*ratio $\frac{\text{CPM DRUG}}{\text{CPM CONTROL}}$

TABLE VII

IMMUNOMODULATING PROPERTIES OF 3-HYDROXY-7,8-DIHYDROTHIAZOLO-[3,2e]-PURINE (NPT 16416): STIMULATION OF MITOGEN INDUCED LYMPHOCYTE PROLIFERATION IN VITRO IN MOUSE SPLEEN CELLS

| COMPOUND (Conc.-ng/ml) | | CPM Incorp. × 10³ | | CPM | | Lo Mitogen D/C* | | Hi Mitogen D/C* | |
|---|---|---|---|---|---|---|---|---|---|
| | | + Con A 375 ng/ml | + Con A 1000 ng/ml | + LPS 5 µg/ml | + LPS 100 µg/ml | Con A | LPS | Con A | LPS |
| NPT 16416 (Ia)- | 0 Control | 19.4 | 59.0 | 1,116 | 7,424 | — | — | — | — |
| | 10 Drug | 17.3 | 61.8 | 1,458 | 8,603 | .85 | 1.30 | 1.04 | 1.05 |
| | 100 Drug | 20.6 | 60.8 | 1,760 | 8,518 | 1.05 | 1.57 | 1.02 | 1.14 |
| | 1,000 Drug | 18.0 | 60.8 | 1,515 | 8,689 | .93 | 1.35 | 1.03 | 1.17 |
| | 2,500 Drug | 19.1 | 54.0 | 1,522 | 7,975 | .98 | 1.36 | .91 | 1.07 |
| | 5,000 Drug | 21.5 | 59.7 | 1,881 | 7,788 | 1.10 | 1.68$^a$ | 1.01 | 1.05 |
| | 25,000 Drug | 22.1 | 59.0 | 2,789 | 11,683 | 1.13 | 2.49$^b$ | 1.0 | 1.57$^c$ |
| | 50,000 Drug | 20.2 | 58.6 | 3,132 | 14,065 | 1.03 | 2.80$^b$ | .99 | 1.89$^b$ |

*ratio $\frac{\text{CPM DRUG}}{\text{CPM Control}}$
$^a p < 0.05$
$^b p < 0.005$
$^c p < 0.025$ The incubation of spleen cells from athymic mice, with NPT 16416 in vitro, resulted in the formation of thymus positive (theta positive) cells. A 125% increase over control values was obtained indicating that NPT 16416 was able to cause the production of T-cells from a T-cell deficient population (in vitro). Levamisole (B) does not possess this property in vitro.

In addition, preliminary toxicity studies using Balb/C mice demonstrated that administration of 50 mg/kg of NPT 16416 (i.p.) resulted in no mortality. If it is assumed 50 mg/kg is the minimum lethal dose and it is assumed <0.05 mg/kg is the minimum effective dose, the lowest possible therapeutic ratio for NPT 16416 is 50/0.05 or 1000/1.0. It is believed that the toxicity is far

TABLE X

IMMUNOMODULATING PROPERTIES OF DIHYDROTHIAZOLO PURINES: COMPARISON OF IN VIVO MODULATION OF ANTIBODY RESPONSE TO SRBC

| COMPOUND | 0.05 | % Change From Control at (mg/kg) 0.5 | 5.0 |
|---|---|---|---|
| NPT 16416 (Ia) | +88*, +226* | +66* | −80* |
| NPT 16485 (IIa) | +28* | +134* | +1.7 (N.S.) |
| NPT 16472 (Ic) | +13$^{a**}$ | — | — |
| NPT 16439 (Ib) | −40%* | −63%$^b$ | — |
| NPT 16449 (IVa) | +183* | +59 | — |

TABLE X-continued
IMMUNOMODULATING PROPERTIES OF DIHYDROTHIAZOLO PURINES: COMPARISON OF IN VIVO MODULATION OF ANTIBODY RESPONSE TO SRBC

| COMPOUND | % Change From Control at (mg/kg) | | |
|---|---|---|---|
| | 0.05 | 0.5 | 5.0 |
| NPT 16450 (IIIa) | −64 | +15 | +36 |

$^a$dose = 0.035 mg/kg
$^b$dose = 0.2 mg/kg
*$p \leq 0.001$
**$p < 0.05$

TABLE XI
IMMUNOMODULATING PROPERTIES OF NPT 16416 (Ia): INDUCTION OF THETA IN SPLENOCYTES FROM ATHYMIC MICE

| COMPOUND (CONC RANGE μg/ml) | PERCENT OF THETA POSITIVE CELLS$^a$ |
|---|---|
| Control (Saline) | 8 |
| Thymic Factor (.01) | 29 |
| NPT 16416 (Ia) (.005-.01) | 14 |
| NPT 16416 (Ia) (.05-.1) | 18 |
| NPT 16416 (Ia) (.5-1.0) | 17 |

$^a$Mean of Three Experiments

The effects of NPT 16416 on stimulating formation of active rosettes when incubated with lymphocytes in vitro from normal volunteers is described in Table XII. It is important to note that $5 \times 10^{-8}$ M concentration of NPT 16416 is capable of producing a 36.5% enhancement of Active E-Rosettes. The enhancement of Active E-Rosettes is biologically important because that fraction of lymphocytes (T-cells) which are the active rosettes are found to be deficient in tumor patients and virus infected individuals. Restoration of this deficiency should benefit the patient.

TABLE XII
IMMUNOMODULATING EFFECT OF NPT 16416: ENCHANTMENT OF E-ROSETTES (ACTIVE)

| COMPOUND (CONC. M) | | % E-ROSETTES (ACTIVE) (x̄) | % INCREASE |
|---|---|---|---|
| Control | | 37 | — |
| NPT 16416 | ($5 \times 10^{-10}$) | 42 | 7.6 |
| NPT 16416 | ($5 \times 10^{-9}$) | 58.5 | 34 |
| NPT 16416 | ($5 \times 10^{-8}$) | 62.5 | 36.5 |
| NPT 16416 | ($5 \times 10^{-7}$) | 55.5 | 23 |
| NPT 16416 | ($5 \times 10^{-5}$) | 43 | 10 |

The subject compounds of this invention have been shown to inhibit the replication of a representative sample of both an RNA (influenza) and a DNA virus (Herpes Virus) using standard tissue culture techniques. In the case of the RNA virus a 48 to 78% inhibition of influenza virus growth was demonstrated in vitro (Table VI) over a concentration range of 0.05–150 μg/ml and in the case of the DNA virus a 33 to 65% inhibition was noted from 37.5–150 μg/ml.

Other members of the RNA and DNA class of viruses are shown in Table A above and are responsible for the diseases specified. In addition a number of viruses have been isolated which cause tumors and thus antiviral agents may have antitumor properties.

It is an established fact that many infectious agents such as viruses (influenza virus, HSV, Friend leukemia virus), bacteria and fungi cause an immune suppressed state in the host, weakening his defenses to infection by infectious agents. Most other antiviral antimetabolite substances, like AraC, cause a suppresion of host immune defense mechanisms, thereby exhibiting potential to lessen the body's own natural defense mechanisms and enhance secondary infection.

An immunopotentiator or immunomodulator is any agent which either restores depressed immune function, or enhances normal immune function, or both. Immune function is defined as the development and expression of humoral (antibody mediated) immunity, cellular (thymocyte-mediated) immunity, or macrophage and granulocyte mediated resistance. It logically includes agents acting directly on the cells involved in the expression of immune response, or on cellular or molecular mechanisms which, in turn, act to modify the function of cells involved in immune response. Augmentation of immune function may result from the action of an agent to abrogate suppresive mechanisms derived by negative feedback influences endogenous or exogenous to the immune system. Thus, immune potentiators have diverse mechanisms of action. Despite the diversity of cell site of action and biochemical mechanism of action of immunopotentiators, their applications are essentially the same; that is, to enhance host resistance.

Applications of Immunopotentiators

1. The principal protective function of the immune system relates to resistance to invasion by pathogens, including viruses, rickettsia, mycoplasma, bacteria, fungi, and parasites of all types. Thus, improvement of immune response, particularly when depressed, would calculatedly improve resistance in infection or infestation by any of the above pathogens. An immunopotentiator alone or in combination with anti-infective therapy can be applied to any and all infectious diseases.

2. A second protective function of the immune system is thought to be resistance to engraftment of foreign tissue, either natural as in the fetal-material relationship; or unnatural as performed by the transplant physician. The use of immunopotentiators to facilitate rejection of fetal or placental tissues or to modify or induce tolerance to grafts is logical.

3. A third protective function of the immune system is thought to be resistance to malignant cell development as in cancer. The use of immunopotentiators in cancer is logical to enhance tumor rejection and to inhibit tumor recurrences following other forms of therapy.

4. A fourth protective function involves the capacity to recognize foreignness and to maintain nonactivity to self by positive suppressor mechanisms. In auto-immune and related disorders, immune reactivity directed at self antigens or exaggerated, elevated responses are apparent which are self destructive. Immunopotentiators would logically be used to restore normal suppressor mechanisms, induce tolerance, or otherwise promote a normal immune response.

Each of the protective functions of the immune system can be modified by nonspecific therapy with immunopotentiators alone or in combination with other agents employed to improve resistance or to kill the invading pathogen. In addition, specific resistance can be augmented by use of immunopotentiators in conjunction with some form of antigen as in a vaccine employing, for example, virus, tumor cell, etc. This use can be to induce either specific immunity or tolerance. The latter might be exemplified by use with antigen in allergy or auto-immune diseases. Use of immunopotentiators may be either therapeutic or prophylatic; the latter particularly in aging, where infection, auto-immune, and cancer are more common. The timing of administration and routes are variable and may be critical in determining whether a positive or negative response results. Any agent capable of augmenting immune response may inhibit it depending on timing and dose; thus, under certain circumstances an immunopotentiator could be used as an immunosuppressive agent for use in allergy, auto-immunity and transplantation.

With the advent of in vitro hybridoma technology and the production of monoclonal antibodies, certain immunopotentiating agents may find application in the modulation of antibody producing B-cell's function to enhance antibody production for commercial purposes. In fact, NPT 16416 and other members of this series (NPT 16485, 16449) have been demonstrated to enhance B-cell proliferation in response to a nonspecific bacterial mitogen (LPS) in vitro (Table VII) as well as the enhancement of production of specific antibodies in vivo, in mice immunized with sheep red blood cells (SRBC) (Tables VIII and IX).

Further, the inhibition of antibody production can be beneficial in auto-immune diseases where the body produces antibodies against itself or in the case of preventing graft rejection. Some members of this series (NPT 16422, 16439) were capable of inhibiting both Con A induced splenocyte proliferation in vitro and antibody production in vivo.

Thus these agents in this series can modulate (enhance or inhibit) the immune response. A detailed description of the types of diseases which modifiers of the B-cell response could be expected to affect in a favorable fashion is set forth below in the section headed "Humoral Immunodeficiencies (B-cell Deficiency)".

The compounds of the invention specifically inhibit the replication of DNA and RNA viruses and modulate the immune response. Based on in vitro and in vivo experiments which demonstrate activity over a concentration range of 0.05 to 150 μg/ml in vitro and 0.05–50 mg/kg in vivo the expected effective dose ranges in mammals is from 0.0005–50 mg/kg.

HUMORAL IMMUNODEFICIENCIES (B-Cell Deficiency)

An increased susceptibility to bacterial infection in the disorders listed in Table 2 usually begins as early as the second half of the first year of life. At that time, a succession of recurrent ear, sinus, skin, and pulmonary infections is often encountered. The patients are also susceptible to septicemia and meningitis. The most frequent bacterial pathogens in these children are the pneumoceoccus, haemophilus influenza, streptococcus, meningococcus, and pseudomonas aeruginosa. Immunity to many viruses appears to be normal, with the exception of the virus causing serum hepatitis. Diagnosis is possible by the analysis of humoral immunity and the clinical picture (Table 1).

TABLE 1

| Humoral Immune Deficiency Syndrome |
|---|
| • Recurrent severe bacterial infections: pneumonitis, meningitis, otitis, septicemia, pydoderma, gastroenteritis: Organisms: pneumoccoccus, streptococcus, meningococcus, pseudomonas, H. influenza |
| • Eczema |
| • Severe form of hepatitis |
| • Malnutrition and failure to thrive |
| • Lymph nodes and tonsils very small |
| • Malabsorption, chronic diarrhea, giardiasis: Complications: arthritis, malabsorption, leukemia, neutropenia, thrombocytopenia, collagen vascular diseases, thyrodites, etc. |

TABLE 2

IMMUNE DEFICIENCY DISEASES
Lymphocyte Defects of Selected Primary Immunodeficiency Syndromes
Affected Lymphocyte Populations

| | T-Cells | | B-Cells | |
|---|---|---|---|---|
| Disorder | Stage 1[1] | Stage 2[1] | Stage 1 | Stage 2 |
| Disorders apparently affecting stem cells | | | | |
| Reticular dysgenesis | yes | yes | yes | yes |
| SCID[2] (thymic alymphoplasia) | yes | yes | (yes)[3] | (yes) |
| SCID (Swiss type) | yes | yes | (yes) | (yes) |
| SCID with ADA deficiency | yes | yes | (yes) | (yes) |
| SCID with ectodermal dysplasia and dwarfism | yes | yes | yes | yes |
| SCID (sporadic) | yes | yes | yes | yes |
| Disorders mainly affecting B-Cells | | | | |
| Congenital hypogammaglobulinemia (Bruton type) | no | no | yes | yes[4] |
| Congenital hypogammaglobulinemia | no | no | yes | yes |
| Common variable immunodeficiency | no | (no) | no | yes[4] |
| IgA deficiency | no | (no) | no | no[4] |
| IgM deficiency | no | no | no | ? |
| IgG subclass deficiency | no | no | no | ? |
| Immunodeficiency with elevated IgM | no | no | no | (yes) |
| X-linked immunodeficiency with normal globulin count or hyperglobulinemia | no | no | (no) | (yes) |
| Hypogammaglobulinemia with thymoma | no | no | no | yes[4] |
| Disorders mainly affecting T-Cells | | | | |
| Thymus hypoplasia (Nezelof's syndrome) | yes | yes | (no) | (no) |
| DiGeorge's syndrome | yes | yes | no | no |
| Nucleoside phosphorylase deficiency | yes | yes | no | no |

TABLE 2-continued
IMMUNE DEFICIENCY DISEASES
Lymphocyte Defects of Selected Primary Immunodeficiency Syndromes
Affected Lymphocyte Populations

| Disorder | T-Cells | | B-Cells | |
|---|---|---|---|---|
| | Stage 1[1] | Stage 2[1] | Stage 1 | Stage 2 |
| Chronic mucocutaneous candidiasis with endocrinopathy | no | yes | no | no |
| Complex immunodeficiencies | | | | |
| Wiskott-Aldrich syndrome | yes | yes | no | (yes) |
| Ataxia-telangiectasia | (yes) | yes | no | (no) |
| Hyper-IgE syndrome | no | yes | no | no |
| Cartilage-hair hypoplasia | ? | yes | no | (no) |

[1]Indicates first or second stages of lymphoid cell differentiation
[2]SCID = severe combined immunodeficiency
[3]Statements enclosed in parentheses indicate defects there are variable in severity or expression
[4]Recent evidence indicates the presence of excessive suppressor cell activity However, the initiation of specific immune responses involve complex series of genetically restricted interactions between macrophage and T-cell subpopulations for CMI and between these cells and B-cells for antibody response. The $T_{Helper}$ and $T_{Suppressor}$ cells exert positive and negative regulatory effects respectively, on B-cell responses. In turn, $I_gM$ and $I_gG$ antibodies may affect the activities of functionally distinct subpopulations of T-cells via their specific receptor for the Fc portion of these classes of immunoglobulin as seen in Table 3.

TABLE 3
Results of Experimental Investigation on Parasite-Induced Immunodeficiency in Rodents*

| Parasite | Antibody Responses | CMI |
|---|---|---|
| Protozoa: | | |
| *Plasmaodium yoelli*** | ↓ | ↓→ |
| *P. berghei*** | ↓ | ↓ |
| *Babesia microti* | ↓ | ↓→ |
| *Toxoplasma gondii* | ↓ | ↓ |
| *Trypanosoma brucei* | ↓ | ↓ |
| *T. congolense* | ↓ | |
| *Leishmania aethiopica* | ↓ | |
| Helminths: | | |
| *Schistosoma mansoni* | ↓ | ↓ |
| *Fasciola hepatica* | ↓ | |
| *Trichinella spiralis* | ↓ | ↓ |
| *Dipetalonema witeae* | ↓ | |

→ = unchanged;
↓ = falls rapidly;
↓→ = variable response
*Antibody deficiencies have usually been investigated by measuring responses to heterologous erythrocytes or soluble antigens. CMI investigations have related to allograft rejection, skin-sensitizing agents, and responses to T-cell mitogens.
**Increased susceptibility to lymphomagenic viruses.

Formulations

The compounds of the present invention can be fed to a mammal at a dosage of 1-1000 mg/kg of body weight and can be anticipated to be active at levels as low as 0.0005 mg/kg.

They may be administered in tablet or capsule form to humans and where solubility permits in the form of aqueous syrups, or as solutions in oils, or where insoluble as a suspension. Typical pharmaceutical formulations are described below:

| Capsule: | |
|---|---|
| NPT 16416 | 0.1-500 mg |
| Avicel pH 101 (microcrystalline cellulose) | to make 800 mg. |

Suspension

Aqueous suspensions can be made with a number of suspending agents incorporated with the active druge substances. Included as suspending agents are such substances as sodium carboxymethylcellulose, Na alginate, gum tragacanth, Avicel RC-591 (microcrystalline cellulose), methylcellulose, Veegum, Xanthan gum. In addition to a suspending agent such substances as sweeteners, flavors, colorants, preservatives, protective colloids, and dispersants may be added.

| SYRUP FORMULATION | |
|---|---|
| NPT 16416 | 0.05-250 mg (or at maximum level of solubility) |
| Corn Sugar | 3.25 g. |
| Distilled Water | .05 g. |
| FD and C Red 40 | .00175 g. |
| Sodium Saccharin | .00250 g. |
| Alcohol U.S.P. | .08 g. |
| Methyl paraben U.S.P. | .005 g. |
| Glycerin | .001 g. |
| Cherry flavor | .31225 g. |
| Fruit flavor | .00825 g. |
| Distilled water g.s.ad | 5 ml. |

| TABLET FORMULATION | |
|---|---|
| NPT 16416 | 0.1-500 mg |
| Avicel pH 101 | 130 mg |
| Starch, modified | 20 mg |
| Magnesium stearate U.S.P. | 5.5 mg |
| Polyvinylpyrrolidone | 22 mg |
| Stearic acid U.S.P. | 30 mg |

Methods

The following procedures were employed in order to make the determination of properties discussed above:

1. Balb/C male mice, 7-8 weeks old, are used up to 20-24 weeks of age.

2. The animals are sacrificed by cervical dislocation and the animals' left sides swabbed with 70% ethanol. An incision is made between the lower ribs and pelvis, laterally from front to back, and the skin retracted. Aseptic technique is to be observed from this point on.

3. The spleen is gently removed with sterile forceps. The fat deposits, are removed and the spleen placed in a sterile 60 mm petri dish containing 3 ml cold, serum-free RPMI-1640; supplemented with antibiotic-antimycotic solution (GIBCO, Cat. #524) and L-glutamine, 2 mM/ml (GIBCO) and placed on crushed ice. When all spleens have been collected and cleaned they are placed in a second petri dish containing 3 ml cold RPMI.

4. Spleen cell suspensions are prepared by gentle mincing of the tissue with a sterile blade and filtering through #100 stainless steel mesh. The remaining tissue is pressed gently with a glass pestle to force out remaining cells and washed with 2-3 ml cold, serum-free RPMI-1640.

5. The cell suspensions are then washed twice in cold RPMI-1640 by centrifuging (1000 rpm, at 4° C. for 30 minutes). The sedimented cell preparation is resuspended in 2 ml (per spleen) RPMI-1640, containing antibiotics, using sufficient agitation to break up any clumped cells.

6. An aliquot of the above suspension is prepared for cell counting as follows: 0.1 ml of suspension is diluted to 1.0 ml with 3% acetic acid and let stand at room temperature for at least five minutes. The sample is then diluted 1:100 with "Isoton II" (Curtis-Matheson Co.) and counted in a coulter counter.

MURINE SPLENOCYTE STIMULATION WITH CONCANAVALIN A (CON A), LIPOPOLYSACCHARIDE (LPS), AND ALLOGENEIC SPLENOCYTES (LMC).

There is set forth below the standard procedure which should be modified according to the solubility and other properties of the particular compound tested.

A. Solutions Preparation

1. Supplemented RPMI-1640
   a. RPMI-1640 (GIBCO)—500 ml bottle(s) stored at 4° C.
   b. HEPES buffer (Flow)—powder stored at 4° C.
   c. AM (Antibiotic-Antimycotic, GIBCO), penicillin 10,000 U/ml, fungizone 25 mcg/ml, streptomycin 10,000 mcg/ml aliquoted in 5 ml and stored at $-20°$ C.
   d. L-glutamine (GIBCO, 200 mM), aliquoted in 5 ml and stored at $-20°$ C.
      Add 5 ml AM and ml L-glutamine to each bottle of RPMI-1640. Add ~10 ml RPMI to 1.79 g HEPES and vortex until completely dissolved. Filter HEPES solution with 10 ml syringe through 0.22 μm Acrodisc filter and add to 500 ml bottle of RPMI-1640. Allow to warm temperature before use.
2. Fetal Calf Serum (FCS, Microbiological associates) aliquoted in 2 ml and stored at $-70°$ C.
3. Mitomycin C (Calbiochem)—50 mg/667 ml supplemented RPMI-1640, aliquoted, and stored at $-70°$ C. Keep tube wrapped in foil until used in assay.
4. PBS (Oxoid Ltd.)—5 tablet/500 ml distilled water, autoclave and store at 4° C.
5. Con A (Calbiochem)—100 mg/ml NaCl injection solution (McGaw), filter, aliquot in 1 ml, and store at $-70°$ C.
6. LPS (Sigma, E. coli serotype #011:84)-~1 mg/ml. Supplement RPMI-1640 with AM and L-glutamine. Remove ~10 ml for dissolving HEPES (0.358 g) and filter HEPES solution. Add four 25 mg bottles of LPS to remaining media and incubate at 37° C. for 1 hour. Filter through 0.22 μm filters, add filtered HEPES, aliquot in 2 ml and store at $-70°$ C.
7. NPT-15392–Add 500 mg/500 ml NaCl injection solution (McGaw), and incubate in 45° C. waterbath for 1 hour. Filter through 0.22 μm filter followed by 0.025 μm filter. Autoclave at 15 psi (250° C.) for 15 minutes. Dilute an aliquot 1:25 in 0.1 N HCl and read absorbance at 250λ on spectrophotometer. Calculate concentration from the following equation:

$$\frac{O.D}{11.42} \times 25 \text{ (or appropriate dilution} \times 278 = \mu g/ml.$$

Aliquot in various volumes and store at $-20°$ C.

8. Tritiated thymidine ($^3$H-TdR, Schwartz-Mann, 6 Ci/mM). Remove a slightly larger volume of $^3$H-TdR than needed from vial with a 1 cc syringe and place volume in the cap of a small sterile plastic tube. Pipet volume necessary for a 1:100 dilution into a tube with appropriate volume of warmed supplemented RPMI-1640 saved from cell assay. Vortex thoroughly before adding to plates. Dispose of all radioactive materials in radioactive container.
9. Toluscint-77 ml Scintiprep/1 gal toluene.

B. Animal Injections

1. Thaw drug to room temperature. Filter through 0.22 μm filter. Dilute in NaCl injection solution to appropriate concentration(s). Aliquot and store at 4° C. until use. On day of use, warm drug to room temperature. Swab animal at area of injection with 70% ethanol and sterile guaze. Inject 0.5 ml i.p. alternating sides each day.

C. Animal Sacrifice and Cell Preparation

1. Animals are sacrificed by cervical dislocation killing one from each group and processing the cells individually before killing the next animal. Swab each animal with 70% ethanol before surgery. Carefully remove the spleen, trimming away any lipid tissue, and place in a 16×125 mm screw-cap tube with a few ml of supplemented RPMI-1640. Use 8 vertical strokes (or enough to break up all tissue) with Teflon-tipped homogenizer. Filter each sample through a 100 mesh screen into a 50 ml tube. Transfer cells into a 15 ml (11×100 mm) tube and fill to top with supplemented RPMI-1640. Centrifuge for 2 minutes at 1700 RPM and resuspend with 5 ml supplemented RPMI-1640. After all samples have been spun, vortex each briefly and let sit for 1 hour. Vortex each sample ~5 seconds, waiting ~10 seconds between each sample. Let sit 5 minutes, then pipet cell suspension into 5 ml (12×75 mm) tube being careful not to remove any sediment. Remove 50 ul cell suspension using micropipetter, carefully wipe pipet tip with kimwipe and pipet into 20 ml Isoton in Coulter counter vial, rinsing pipet several times in the Isoton. Add 6 drops of CyMet and swirl vial to mix. Use the following Coulter counter settings: Amplification-1, Threshold-10, and Aperture Current-1. Clean counter with Isoterge the morning of experiment and count background before standardizing with CH. 60 Hematology Controls. After cell counts are obtained, dilute to 6×10$^6$ cells/ml with supplemented RPMI and aliquot into 3 tubes for the 3 assays.

D. Mitogen Assays

1. Pipet 100 μl control media (supplemented RPMI) or appropriate dilution of mitogen (starting with lowest concentration) into microtiter plate using Titertek multi-channel pipetter. Place plates in 37° C. CO$_2$ incubator with CO$_2$ set at 0.5 after each plate has been pipetted. Pipet 100 μl responder cells into wells starting with most dilute mitogen concentration. Place plates in incubator as they are filled and after all plates are in incubator, let sit for 10-20 minutes. Wrap plates with plastic wrap, recover with top, replace in incubator, and reset $CO_2$ to ~0.05. Save ~50 ml supplemented RPMI at 4° C. for thymidine dilution. After ~44 hours warm the RPMI to 37° C. in incubator. Dilute tritiated Thymidine 1:100 in warmed RPMI. Use Titertek to add 50 μl Thymidine to each well. Treat plates as above and incubate overnight (~18 hours).

E. Cell Harvest

1. Rinse lines of cell harvester well before harvesting plates. Using a new filter strip for each row, wash each row 20 times with saline and 20 times with water. Place strips on labeled styrofoam (foamed polystyrene) board and dry under infrared lamp for ~1 hour. Cut out sample discs on disc-cutter into scintillation vials, add ~2 ml toluscint with automatic dispenser, and cap vials while still in the metal tray. Put vials in scintillation counter and count.

F. MLC Cell Preparation

1. Use responding cells prepared for Con A and LPS assays and prepare allogeneic cells with C57BL/6 mice. Kill animals and homogenize cells as in step C. Transfer cells into 15 ml Falcon tube (11×100) and fill to top with RPMI-1640 medium. Centrifuge for 1½ minutes at 1,700 RPM. Do another wash at 1,700 RPM for 1½ and resuspend in 2 ml of RPMI-1640. Pool the cells from all allogeneic mice. Let the clumps settle on the bottom of the tube for five minutes. Carefully remove the supernate from the clumps of cells.

2. Perform a cell count as in step C and dilute cells to give $180 \times 10^6$ cells/6 ml of RPMI medium.

3. While vortexing, add 0.2 ml of MitC to the cells. Incubate at 37° C. with 5% $CO_2$ for 30 minutes. During incubation, mix the cells gently every 10 minutes.

4. At the end of 30 minutes incubation, dilute the cells with RPMI-1640 medium to top of 15 ml Falcon tube. Centrifuge at 1,700 RPM for 1½ minutes. Pour supernate off and remove the last few drops by touching the edge of the tube on a piece of sterile gauze.

5. First wash: Add 3-5 ml of RPMI medium and vortex at setting #3 for 10-20 seconds. Fill the tube with RPMI-1640 medium and centrifuge at 1,700 RPM for 1½ minutes.

6. Second wash: Pour supernate off and touch edge of tube on sterile gauze to remove last few drops. Add 3-5 ml of RPMI and vortex at #3 setting for 10-20 seconds. Fill the tube with RPMI-1640 to the top and let set for 15 minutes, then centrifuge at 2,000 RPM for 2 minutes.

7. Third wash: Repeat the second wash. Resuspend in 5 ml of RPMI-1640.

8. Dilute Allogeneic cells to $6 \times 10^6$ cells/ml or $48 \times 10^6$ C/8 ml.

9. Use responding cells of $6 \times 10^6$ cells/ml prepared for Con A and LPS assay.

10. Cell Plating: For each individual animal, plate 2 rows of 3 or 4 wells on 96 well costar plate. First row for Control use 100λ of responding cells and 100λ of RPMI-1640 (supplemented). The second row use 100λ of responding cells and 100λ of Allogeneic cells.

11. Procedure for incubation, labeling with tritiated thymidine, and harvesting the cells are the same as for Con A and LPS assays except for the incubation before labeling time with $^3H$ Thymidine which is 68 hours after cell plating instead of 44 hours. Cell harvesting is done at the usual 18 hours after labeling with $^3H$ Thymidine.

There is set forth below the standard procedure which should be modified according to the solubility and other properties of the particular compound tested.

A. Preparation of NPT Drug Solutions

1. A solution containing 500 μg/ml NPT is prepared by adding a preweighed amount of the drug powder to sterile PBS (phosphate buffered saline) and sonicating the solution for 30 minutes.

2. The wavelength of GCA/McPherson double beam spectrophotometer is set to the λ max.

3. The NPT is diluted 1:10 with 0.1 normal HCl.

4. Fifteen ml of 0.1 normal HCl is poured into beaker. This solution is used to rinse cuvettes. Both cuvettes are filled with 0.1 normal Hcl and the wavelength is read. Absorbance should be within 0.001-0.005 from the zeroed value.

5. The sample cuvette is emptied and the diluted drug solution is added.

6. Absorbance is recorded and concentration is calculated as follows:

Formula:

$$\frac{\mu g}{ml} = \frac{A(\text{absorbance}) \times \text{Dilution Factor} \times \text{Molecular Weight}}{\epsilon(\text{Millimolar Absorptivity})}$$

B. Prior to Day 0

1. NPT drug solution is made by dissolving 500 μg NPT per ml PBS.

2. The concentration is checked according to section A of this SOP.

3. The stock is aliquoted into 1 ml samples and stored at −20° C. for several months.

4. Solutions are thawed and diluted to desired concentration.

C. Agarose Base Plates are Made as Follows:

1. A 1.4% suspension of agarose in PBS (7 g in 500 ml) is autoclaved for 15 min.

2. Using a Cornwell syringe, 3 ml volumes of molten agarose are aseptically dispensed into Falcon #1006 petri dishes and swirled to form an even layer.

3. These plates may be stored up to one week at 4° C. prior to use. The plates are stored in an inverted position (agar on top of plate).

D. Preparation of Guinea Pig Serum

1. Ten ml of blood is removed by cardiac puncture from two to six guinea pigs and placed in a 50 ml Falcon #2070 centrifuge tube without anticoagulants.

2. These tubes are incubated for 45 min. at 37° C. for clot formation.

3. Tubes are then removed from incubator and put on ice for 30 min. to retract the clot.

4. The serum is aseptically poured off each tube, pooled, dispensed into 1 ml aliquots and stored at −70° C. until used.

E. Immunization, Day 0

1. Mice are immunized as follows: sheep blood (sheep #23) is received weekly from Hyland labs. It is asceptically collected in two volumes of Alseviers to one volume of blood.

2. Five-tenths ml of the sheep blood in Alseviers is washed three times in sterile PBS in an IEC clinical centrifuge, setting #4 (2800 RPM) for 10 min. at room temperature.

3. The pellet is resuspended in 1:10 in sterile PBS.

4. A model Z Coulter counter is calibrated according to Coulter instruction Manual.

5. A 1:100,000 dilution is needed for a Coulter counter cell count and is obtained by first making a 1:100 dilution in PBS and then diluting this solution 1:100 is isoton. The Coulter counter threshold is adjusted to setting #5.

6. The cell count is determined and the stock solution is diluted to $4 \times 10^7$ cells/ml. This final suspension is used for immunization.

7. Each mouse is immunized by i.v. injection into the lateral tail vein (warmed in a 50° C. water bath for veinous dilation) with 0.1 ml SRBC (sheep red blood cell) suspensions; the final concentration of SRBC's is $4 \times 10^6$ per mouse.

F. Treatment

1. Mice are treated by i.p. injection on days 9, 1, 2, and 3. A syringe (1 cc) is fitted with a one-half inch, 26 gauge needle. The needle is introduced at a 45° angle along the right side of the linea alba. A 0.2 ml volume is given to both drug and control treated groups.

2. Drug groups are given 0.2 ml of a desired concentration NPT solution which, for a 20 g mouse, is 5 µg/ml.

G. Spleen Preparation, Day

1. Spleens are removed aseptically and placed individually in Falcon #2025 tissue culture tubes containing 3 ml MEM. The tubes are then stored on ice.

2. Spleens are homogenized in the same tube with a teflon pestle attached to a G. K. Heller variable speed reversible motor connected with a G. K. Heller GT-21 motor controller setting #6.

3. The homogenization time and action should be uniform from sample to sample.

4. Samples are then filtered through a 100 mesh 40 micron stainless steel screen into a standard tissue culture tube. The screen is rinsed with 3 ml MEM and the cell suspension is stored on ice.

5. A 1:1000 dilution is made for a Coulter counter cell count and is obtained by first making a 1:100 dilution in PBS followed by a 1:10 dilution in isoton.

6. The cell count is obtained and the stock suspension is diluted to $1 \times 10^7$ cells/ml. The Coulter counter threshold is set at 10. Red cells are lysed with three drops of Zap isoton.

H. Preparation of Top Agar (0.7%)

1. Thirty-five hundredths gram agarose and 0.53 gram MEM powder are placed into an Erlenmeyer flask. Fifty ml of distilled $H_2O$ is then added to the flask.

2. The solution is autoclaved for 15 min. at 250° F. and 15 psi. It is then placed in a 45° water bath for 5 min. The pH is adjusted to approximately 7.2 by the addition of sodium bicarbonate (0.1 ml $Na_2CO_3$).

3. One ml aliquots are dispensed into 5 ml tissue culture tubes previously placed in the water bath. Allow several extra tubes for replacement in case of plating error.

I. Preparation of 10% SRBC Solution

1. Five ml sheep blood (same batch as used for immunization) is washed three times in PBS using an IEC Clinical Standard Centrifuge, speed #4 (2800 RPM) for 10 min.

2. After the third wash, the cells are resuspended in a volume of PBS ten times the volume of the packed cells, i.e. 0.5 ml of packed SRBC's, Q.S. to 5 ml with PBS.

J. Plating

1. Agar plates are removed from refrigerator and allowed to warm to room temperature. They are labeled in triplicate for each experimental group.

2. Agar-filled tubes are removed from the water bath. One-tenth of the 10% SRBC's and 0.1 ml spleen cell suspension are added to each agar tube. The tubes are agitated on a Vortex mixer.

3. The contents of the tubes are poured immediately into agar base plates and swirled until a smooth layer is formed. The plates are placed on a level surface until the agar solidifies.

4. The plates are incubated at 37° C. in a humidified atmosphere of 5% $CO_2$ and 95% air for 90 min.

5. Guinea pig complement (see preparation, section D) is removed from freezer, thawed at room temperature and diluted 1:10 in PBS.

6. Plates are removed from incubator and 1 ml of the diluted complement is added to each plate.

7. Plates are then incubated another 30–45 minutes at 37° C. Plates are then removed from incubator and counted using oblique light.

8. Plates can be stored at 4° C. in an inverted position and counted up to 24 hours later.

What is claimed is:

1. A compound having one of the formulae

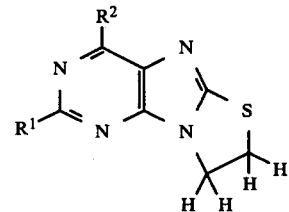

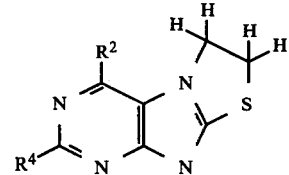

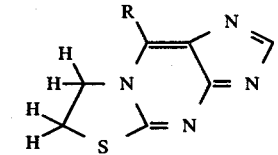

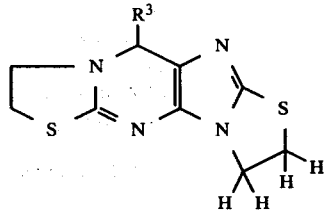

where $R^1$ is hydrogen, lower alkylthio, lower alkylsulfinyl, amino or halogen, $R^2$ is hydroxy, lower alkylthio, halogen, or mercapto, R is hydroxy, mercapto, lower alkylthio or halogen, $R^3$ is hydroxy, mercapto, lower alkylthio, halogen, or amino, $R^4$ is lower alkylthio, lower alkylsulfinyl, amino, halogen or hydrogen.

2. A compound according to claim 1 wherein when $R^1$, $R^2$, $R^3$, or R is lower alkylthio, it is methylsulfinyl and when $R^1$ is lower alkylsulfinyl it is methylthio.

3. A compound according to claim 1 wherein $R^2$, R and $R^3$ are hydroxy.

4. A compound according to claim 3 wherein $R^1$ is hydrogen.

5. A compound according to claim 1 having formula I.

6. A compound according to claim 5 where $R^1$ is hydrogen or methyl mercapto and $R^2$ is hydroxy or methyl mercapto.

7. A compound according to claim 6 where $R^2$ is hydroxy.

8. A compound according to claim 7 where $R^1$ is hydrogen.

9. A compound according to claim 1 having formula II.

10. A compound according to claim 9 where $R^2$ is hydroxy.

11. A compound according to claim 10 where $R^4$ is fluorine.

12. A compound according to claim 1 having formula III.

13. A compound according to claim 12 where R is hydroxy.

14. A compound according to claim 1 having formula IV.

15. A compound according to claim 14 where $R^3$ is hydroxy.

16. A compound according to claim 1 wherein $R^1$ is hydrogen, lower alkylthio, lower alkylsulfinyl or halogen, $R^3$ is hydroxy, mercapto lower alkylthio or halogen and $R^4$ is lower alkylthio or lower alkylsulfinyl.

17. A compound according to claim 16 having formula I where $R^2$ is hydroxy and $R^1$ is hydrogen, lower alkylthio, lower alkylsulfinyl or halogen.

18. A compound according to claim 1 having formula I where $R^2$ is lower alkylthio or mercapto.

19. A compound according to claim 1 having the formula I where $R^2$ is halogen.

20. A compound according to claim 1 having formula II where $R^4$ is lower alkylthio, lower alkylsulfinyl, halogen or hydrogen.

21. A compound according to claim 20 wherein $R^4$ is lower alkylthio, lower alkylsulfinyl or halogen.

22. A compound according to claim 1 having formula II where $R^2$ is lower alkylthio, halogen or mercapto.

23. A compound according to claim 22 where $R^2$ is lower alkylthio or mercapto.

24. A compound according to claim 1 having formula II where $R^4$ is lower alkylthio, lower alkylsulfinyl, amino halogen or hydrogen.

25. A compound according to claim 24 where $R^2$ is hydroxy.

26. A compound according to claim 25 where $R^4$ is hydrogen.

27. A compound according to claim 24 where $R^2$ is hydrogen, lower alkylthio, or lower alkylsulfinyl.

* * * * *